United States Patent
Drake, Jr.

(10) Patent No.: US 7,208,749 B2
(45) Date of Patent: Apr. 24, 2007

(54) SYSTEM AND METHOD FOR LOCATING AND POSITIONING AN ULTRASONIC SIGNAL GENERATOR FOR TESTING PURPOSES

(75) Inventor: Thomas E. Drake, Jr., Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 189 days.

(21) Appl. No.: 10/645,404

(22) Filed: Aug. 21, 2003

(65) Prior Publication Data
US 2004/0036042 A1 Feb. 26, 2004

Related U.S. Application Data

(63) Continuation of application No. 09/907,493, filed on Jul. 16, 2001, now Pat. No. 6,643,002.

(60) Provisional application No. 60/218,340, filed on Jul. 14, 2000.

(51) Int. Cl.
*G01B 11/24* (2006.01)
(52) U.S. Cl. .......................... 250/559.22; 250/559.28; 250/559.38; 356/608
(58) Field of Classification Search ........... 250/559.22, 250/559.23, 559.27, 559.29, 559.31, 559.38; 356/2, 72, 73, 600–602, 606–608, 614; 73/620, 73/655
See application file for complete search history.

(56) References Cited

U.S. PATENT DOCUMENTS 3,911,733 A 10/1975 Bhuta et al. ................... 73/88
3,992,627 A 11/1976 Stewart ....................... 250/312
4,349,112 A 9/1982 Wilks et al. ................ 209/538

(Continued)

OTHER PUBLICATIONS

NTIAC Newsletter; vol. 27, No. 5, Sep. 2002, 5 pp.

(Continued)

*Primary Examiner*—Stephone B. Allen
(74) *Attorney, Agent, or Firm*—Garlick, Harrison, Markison; Robert McLauchlan

(57) ABSTRACT

The invention is directed to an ultrasonic testing system. The system tests a manufactured part for various physical attributes, including specific flaws, defects, or composition of materials. The part can be housed in a gantry system that holds the part stable. An energy generator illuminates the part within energy and the part emanates energy from that illumination. Based on the emanations from the part, the system can determined precisely where the part is in free space. The energy illumination device and the receptor have a predetermined relationship in free space. This means the location of the illumination mechanism and the reception mechanism is known. Additionally, the coordinates of the actual testing device also have a predetermined relationship to the illumination device, the reception device, or both. Thus, when one fixes the points in free space where the part is relative to either of the illumination device or the reception device, one can fix the point and/or orientation of the testing device to that part as well. It should be noted that the results of the point and/or orientation detection may also be used in an actuator and control system. If the position of the testing device needs to be altered with respect to the tested object, the control system and actuator may use the results of this determination to move the testing device relative to the tested object.

8 Claims, 7 Drawing Sheets

U.S. PATENT DOCUMENTS

| | | | | |
|---|---|---|---|---|
| 4,355,538 | A | 10/1982 | Hall | 73/811 |
| 4,422,177 | A | 12/1983 | Mastronardi et al. | 378/17 |
| 4,581,939 | A * | 4/1986 | Takahashi | 73/643 |
| 4,803,639 | A | 2/1989 | Steele et al. | 364/507 |
| 4,809,308 | A | 2/1989 | Adams et al. | 378/99 |
| 4,841,460 | A | 6/1989 | Dewar et al. | 364/571.02 |
| 5,014,293 | A | 5/1991 | Boyd et al. | 378/197 |
| 5,065,630 | A | 11/1991 | Hadcock et al. | 73/802 |
| 5,113,079 | A | 5/1992 | Matulka | 250/550 |
| 5,119,408 | A | 6/1992 | Little et al. | 378/4 |
| 5,122,672 | A | 6/1992 | Mansour | 250/571 |
| 5,140,533 | A | 8/1992 | Celette | 364/559 |
| 5,295,073 | A | 3/1994 | Celette | 364/424 |
| 5,319,567 | A | 6/1994 | Ebenstein | 364/474.34 |
| 5,384,717 | A | 1/1995 | Ebenstein | 364/560 |
| 5,442,572 | A | 8/1995 | Kiridena et al. | 364/560 |
| 5,486,063 | A * | 1/1996 | Fox et al. | 400/708 |
| 5,490,195 | A | 2/1996 | Berkley | 378/72 |
| 5,491,333 | A * | 2/1996 | Skell et al. | 250/222.1 |
| 5,541,856 | A | 7/1996 | Hammermeister | 364/552 |
| 5,552,984 | A | 9/1996 | Crandall et al. | 364/424.03 |
| 5,574,226 | A | 11/1996 | Reuther et al. | 73/669 |
| 5,637,812 | A | 6/1997 | Baker et al. | 73/865.6 |
| 5,760,904 | A * | 6/1998 | Lorraine et al. | 356/513 |
| 5,848,115 | A | 12/1998 | Little et al. | 378/4 |
| 5,867,604 | A * | 2/1999 | Ben-Levy et al. | 382/254 |
| 6,023,985 | A | 2/2000 | Fournier | 73/865.6 |
| 6,047,041 | A | 4/2000 | Ellinger | 378/58 |
| 6,205,240 | B1 | 3/2001 | Pietrzak et al. | 382/152 |
| 6,220,099 | B1 | 4/2001 | Marti et al. | 73/633 |
| 6,335,943 | B1 * | 1/2002 | Lorraine et al. | 372/28 |
| 6,360,621 | B1 | 3/2002 | Eldred et al. | 73/865.6 |
| 6,378,387 | B1 | 4/2002 | Froom | 73/865.8 |
| 6,466,643 | B1 | 10/2002 | Bueno et al. | 378/58 |
| 6,571,008 | B1 | 5/2003 | Bandyopadhyay et al. | 382/154 |
| 6,637,266 | B1 | 10/2003 | Froom | 73/583 |
| 2003/0133129 | A1 * | 7/2003 | Yagi et al. | 356/602 |

OTHER PUBLICATIONS

Froom, Douglas A., et al.; Solving Problems with Advanced Technology, 1999 IEEE, 4 pp.

Alkire, M.G., Department of the Air Force Memo regarding Construction Project Data; May 7, 1982, Bates 000010 through Bates 000068.

U.S. Air Force, Military Construction Project Data, Apr. 14, 1982, Bates 000074 though Bates 000129.

U.S. Air Force, Attachment I to Request for Environmental Impact Analysis, Dec. 2, 1982, Bates 000130 through Bates 000167.

Stanghellini, Frank D., Department of the Air Force Memo regarding Criteria Changes, Jan. 9, 1985, Bates 000168 through Bates 000214.

Metro Today, The Sacramento Union; May 12, 1983, Bates 000215 through Bates 000216.

Letter Contract Between Department of the Air Force and Par Systems Corp., Aug. 3, 1984, Bates 000217 through Bates 000312.

Timeline and Equipment List for Contract Between Department of the Air Force and Par Systems Corp., Aug. 3, 1984, Bates 000313 through Bates 000325.

Spacemaker, Jun. 19, 1997, Bates 000326 through 000327.

Civilian Personnel Position Description, Department of the Air Force; Jul. 10, 1989, Bates 000328 through Bates 000332.

Aviation Week & Space Technology, Mar. 13, 1989, Bates 000333 through Bates 000336.

UltraOptec, Laser Ultrasonic System, 1999 IEEE, Bates 000337 through Bates 000340.

J.W. Bader, et al., Laser Ultrasonics or Alternative NDI Composite Defect, Nov. 20, 1990, Bates 000342 through Bates 000446.

Douglas A. Froom, Statement of Work for Advanced Ultrasonic Component Inspection System, Jul. 14, 1993, Bates 000447 through 000490.

Award of Contract form Department of the Air Force, Aug. 11, 1993, Bates 000491 through Bates 000492.

UltraOptec, LUIS Phase 3 Acceptance Test Report, Feb. 16, 1996, Bates 000493 through Bates 000501.

Spacemaker, Feb. 22, 1996, Bates 000502.

* cited by examiner (CONTINUED FROM PREVIOUS PAGE)
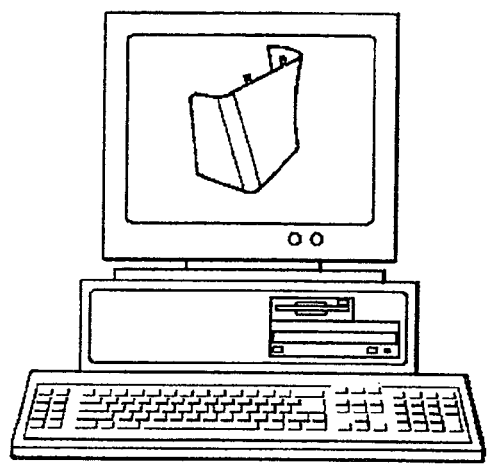
FIG. 9
(CONTINUED)
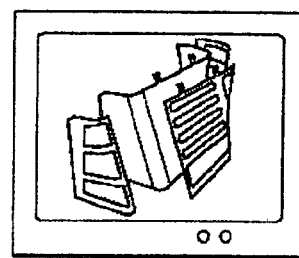
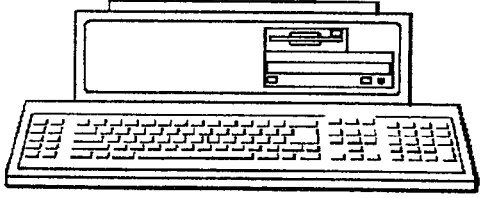
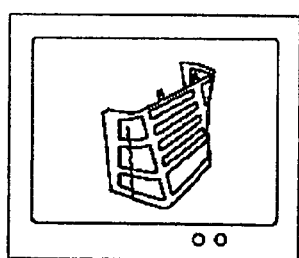
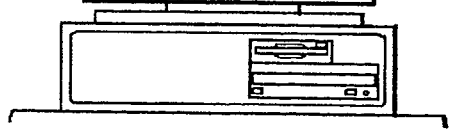

SYSTEM AND METHOD FOR LOCATING AND POSITIONING AN ULTRASONIC SIGNAL GENERATOR FOR TESTING PURPOSES

RELATED APPLICATIONS

This application claims priority of and is a continuation of U.S. patent application Ser. No. 09/907,493, filed Jul. 16, 2001 now U.S. Pat No. 6,643,002 entitled "SYSTEM AND METHOD FOR LOCATING AND POSITIONING AN ULTRASONIC SIGNAL GENERATOR FOR TESTING PURPOSES,", and is incorporated herein by reference in its entirety.

This application claims priority of U.S. Provisional Application Ser. No. 60/218,340, filed Jul. 14, 2000 entitled "Remote Laser Beam Delivery System and Method for Use with a Robotic Positioning System for Ultrasonic Testing Purposes,", and is incorporated herein by reference in its entirety.

Additionally, this application is related to and incorporates by reference U.S. patent application Ser. No. 09/416,399 filed on Oct. 10, 1999 entitled "METHOD AND APPARATUS FOR DETECTING ULTRASONIC SURFACE DISPLACEMENTS USING POST-COLLECTION OPTICAL AMPLIFICATION" to Thomas E. Drake.

TECHNICAL FIELD OF THE INVENTION

The present invention relates generally to a system and method for locating and positioning an ultrasonic signal generator with respect to a tested part. In particular, the invention is directed to a system and method for delivering a laser beam generated by a laser source to a particular point on a tested object, or for determining a precise point on the object the ultrasonic signal generator delivered the energy to, in a gantry positioning system for use in detecting material defects of a test object using ultrasonic techniques.

BACKGROUND OF THE INVENTION

This application claims priority of U.S. Provisional Application Ser. No. 60/218,340, filed Jul. 14, 2000 entitled "Remote Laser Beam Delivery System and Method for Use with a Robotic Positioning System for Ultrasonic Testing Purposes,", and is incorporated herein by reference in its entirety.

Additionally, this application is related to and incorporates by reference U.S. patent application Ser. No. 09/416,399 filed on Oct. 10, 1999 entitled "METHOD AND APPARATUS FOR DETECTING ULTRASONIC SURFACE DISPLACEMENTS USING POST-COLLECTION OPTICAL AMPLIFICATION" to Thomas E. Drake.

It is desirable for a variety of applications to provide for mechanically directing a laser beam to any location within a predetermined volume or on a surface. Many of these applications are tailored specifically for use within industrial manufacturing applications employing automated, robotics systems. Over the past several decades, the advent of robotics and laser light source technologies have led to many integrated systems for assembly line manufacturing. For example, robotics assembly systems incorporating laser technologies are very typical in automobile and even aircraft manufacturing plants for performing such tasks as welding.

For many systems, a robotic or gantry positioning system having a mechanical armature is often used to direct a laser beam to a variety of locations of a single workpiece. This armature itself provides for precision directing of the laser beam from the end of the mechanical armature. A laser beam delivery system is normally integrated into the gantry positioning system (GPS), particularly into the mechanical armature, for directing the laser beam from the end of the mechanical armature to any location within a predetermined volume. Specifically, the laser beam is then directed to portions of a workpiece and often from various fields of view for welding, cutting, ablating, or any variety of applications employing a laser beam.

Ultrasonic testing is a method which may be used to detect material defects in a objects comprised of various materials. A common application for ultrasonic testing is to detect inhomogeneities in composite materials. Ultrasonic testing may be used to serve a variety of industrial needs including identification of defects in manufactured goods for tuning of manufacturing processes. Manufacturers of products comprising composite material may wish to identify imperfections in their articles of manufacture to modify their manufacturing process to strive for greater repeatability and efficiency in their process or simply to identify problem areas within their process. Composite materials comprise many critical components within modern, high performance aircraft, and are becoming more common in terrestrial applications such as the automotive industry. Composite materials are desirable for many of their inherent attributes including lightweight, high strength, and stiffness. Particularly for aircraft application, those composite material components, which may be large and complex in shape, are often flight critical necessitating strict assurance of material and structural integrity.

Unfortunately, these materials are sometimes fabricated with imperfections or develop them after several hours of use. These material defects may appear as a delamination of the surface of the material, porosity, an inclusion, debonds between bonded sub-components, or a void within the component itself. This inhomogeneity in the structure severely weakens it, providing a situation which might result in catastrophic failure. A conventional method for detecting material defects in a composite material utilizes piezoelectric transducers in conjunction with mechanical scanners mounted across the surface of the composite to detect any material imperfections. The disadvantages of the conventional methods are many, including difficulty in accommodating non-flat or evenly mildly contoured composite materials. Another disadvantage is the requirement that the transducer couple to the material via a water path. The transducer must remain normal to the surface within ±3° during a scan. To accommodate highly contoured and complex shaped components using conventional techniques often requires extremely time-intensive test set up preparation.

Laser ultrasonic testing is an alternative method that is used to identify these imperfections. For aircraft applications, particularly for military fighter aircraft, all flight critical parts fabricated of composite material must be fully inspected before installation. A GPS comprising a laser beam delivery system may be integrated with a laser ultrasonic testing system for providing automated identification of material defects of a test object.

One approach is to mount the laser ultrasonic testing system comprising a laser source on the end of the mechanical armature of the GPS. The use of a GPS allows the ultrasonic testing system to be maneuvered around the test object to provide for positioning the laser source in close proximity to the test object from a multitude of locations of fields of vision. For those ultrasonic testing systems which use high power gas lasers such as $CO_2$ lasers, the large and bulky size of the laser complicates the integration of the ultrasonic testing system with the GPS as the end segment of the mechanical armature must be capable of supporting a significantly heavy weight at its end. The large size and bulky weight of the light source itself often demands the use of a very large GPS capable of supporting the heavy weight of an ultrasonic testing system as it is maneuvered around the test object to perform data acquisition from a variety of perspectives.

Many typical laser testing systems are hampered when the ultrasonic energy generator is not positioned properly relative to the part to be tested. When this happens, the test results may need to be corrected, or in the case of testing relative strengths of different parts, this test may be completely inconclusive. Further, when the ultrasonic signal is generated, the resulting ultrasonic signal affects certain areas and/or volumes of the tested object. To completely test an object requires that a signal ultrasonic event be generated many times throughout various places on the surface and interior to the object. By doing this numerous times, the complete object may be tested, even though some areas affected may be common to others. In this case, many systems that rely on manual positioning err on a conservative side. This results in hugely overcompensated testing of the part since the overlaps are huge. Precise positioning of the ultrasonic testing device allows for scalable and efficient economies in the testing process, since the area of overlaps may be minimized.

SUMMARY OF THE INVENTION

The present invention employs a laser ultrasonic testing system which is used to identify and detect material defects in a test object. Data is acquired of the test object and is analyzed for identifying any material defects in the test object and for providing the precise locations of them. Identifying material defects in composite materials, particularly those within aircraft applications, may provide aircraft designers with information concerning actual life and fatigue of flight critical, composite components as well as provide manufacturers of composite components with information concerning stress and failure points of the component. The ultrasonic testing system within this invention is provided and presented in detail in U.S. patent application Ser. No. 09/343,920 entitled "System and Method for Laser Ultrasonic Testing" by T. E. Drake, Jr.

Aspects of the invention are found in an ultrasonic lasing system. The laser system tests a manufactured part for various physical attributes, including specific flaws, defects, or composition of materials. The part can be housed in a gantry system that holds the part stable. An energy generator illuminates the part within energy and the part emanates energy from that illumination. Based on the emanations from the part, the system can determined precisely where the part is in free space. The energy illumination device and the receptor have a predetermined relationship in free space. This means the location of the illumination mechanism and the reception mechanism is known. Additionally, the coordinates of the actual testing device also have a predetermined relationship to the illumination device, the reception device, or both. Thus, when one fixes the points in free space where the part is relative to either of the illumination device or the reception device, one can fix the point and/or orientation of the testing device to that part as well.

It should be noted that the results of the point and/or orientation detection may also be used in an actuator and control system. If the position of the testing device needs to be altered with respect to the tested object, the control system and actuator may use the results of this determination to move the testing device relative to the tested object.

To do this, either the tested object needs to be moved within the gantry system, or the testing device needs to be moved relative to the tested object. Of course, these actions may occur in combination. This may be accomplished with a computer that assists in determining the position and/or orientation. This may be used to control the relative movement of the object and testing device.

The system may also be used not to precisely position a testing device relative to an object, but may be used for compensation purposes as well. In this embodiment, the testing system tests the object, then the positioning system determines the relative position of the object to the position and/or orientation of the testing device. When the position and/or orientation of the testing device relative to the tested object is not exact, a CAD representation of the object may be used to derive corrections based on incorrect orientation and/or positioning aspects of the system.

The generating energy may be of various sorts. This includes electromagnetic as well as sonic. In the case of an electromagnetic system, various forms of this energy may be used as well. For example, the generator may generate radar waves and the receptor may detect these reflected radar waves. Or, the generator may generator coherent energy, such as a laser, that bathes the object. The reception apparatus may be a camera or other optical receiver such as a photoelectric detector. In this case, the various lightings, and optical characteristics of the light receptor, such as focal point of the receptor, allow one to determine the spatial orientation of the generating device and the receiving device in space relative to the object. Or, another energy, such as sonic energy, may be used in a sonar-type system.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE PREFERRED EMBODIMENT

Preferred embodiments of the present invention are illustrated in the FIGURES, like numerals being used to refer to like and corresponding parts of the various drawings.

The present invention employs a gantry positioning system with an integral laser beam delivery system for delivering a laser beam delivered by a remote laser source to a test object for performing ultrasonic testing to detect any material defects in the test object. The gantry positioning system provides for scanning the entire test object from various fields of view to map out the test object using laser ultrasonic techniques. Data are recorded from all of the fields of view and later processed to provide for not only the detection of any such material defects, but also their location within the test object.

Figure 1:
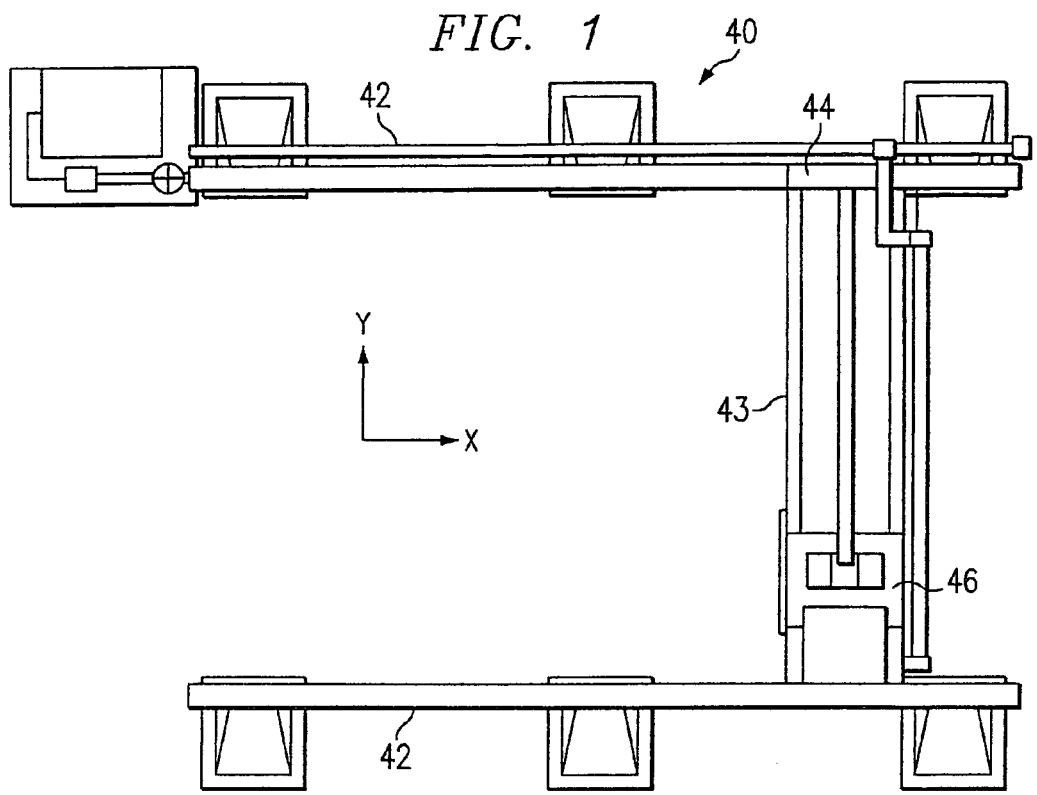
FIG. 1 shows one embodiment of a gantry positioning and ultrasonic testing system with an integral laser beam delivery system.

FIG. 1 shows one embodiment 30 of a gantry positioning and ultrasonic testing system with an integral laser beam delivery system. A laser beam 11 is generated by a remote laser source 31 and inserted into the optical transmission channel of a first gantry member 32. Each gantry member of the gantry positioning system comprises an optical alignment system similar to that described in FIG. 2 for guiding the laser beam 11 through the gantry positioning system and for delivering it to a test object 35 for performing ultrasonic testing. The gantry positioning system is comprised of a number of gantry members pivotally connected. At each of these pivotal connections is a gantry actuator 33 for controlling the shape of the gantry positioning system which provides for positioning the end gantry member 34 to any location within the desired workspace in which the test object 35 is located. By permitting the gantry positioning system to be manipulated around the workspace of the test object 35 allows for performing ultrasonic testing using an ultrasonic testing system 36 from a variety of fields of view. Additionally, a laser beam conditioning system 37 may be used to provide for minimizing the divergence of the laser beam 11 as it exits the end gantry member 34 of the gantry positioning system and is delivered to the test object 35. The laser beam conditioning system 37 could likewise be included within the optical transmission channels 22 of the gantry segments of the GPS to provide for conditioning and minimizing the divergence of the beam as it propagates through the GPS.

Figure 2:
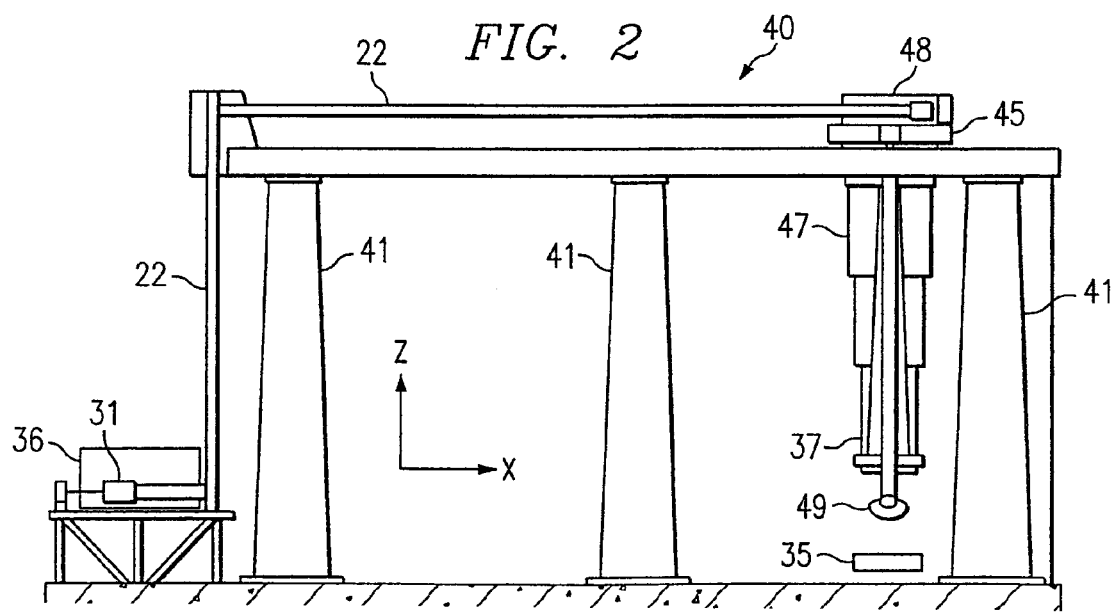
FIG. 2 shows a particular embodiment of FIG. 1 of gantry positioning and ultrasonic testing system with an integral laser beam delivery system.

FIG. 2 shows a particular embodiment 40 of FIG. 1 of a gantry positioning and ultrasonic testing system with an integral laser beam delivery system. The gantry positioning system is comprised of a plurality of vertical supports beams 41 which support two runway beams 42 which run parallel to one another. A bridge beam 43 spans between the two runway beams and is powered using a bridge beam actuator 44 for providing translation in a first direction, depicted as the X direction in the TOP VIEW shown in FIG. 2. A carriage 45 is mounted on top of the bridge beam 43 and is powered using a carriage actuator 46 for providing translation in another direction which is orthogonal to the first direction. This second direction is depicted as the Y direction in the TOP VIEW shown in FIG. 2. Extending downward from the bridge beam 43 is a Z-mast 47, whose length is variable and is controlled using a Z-mast actuator 48. The Z-mast provides for translation in a third direction, orthogonal to the first two directions. This third direction is depicted as the Z direction in the SIDE VIEW shown in FIG. 2.

By providing movement in three orthogonal positions and delivering a laser beam throughout the system, the particular embodiment shown in FIG. 2 of a gantry positioning system provides for emitting the laser beam 11 at any location within the workspace of the test object 35 allows for performing ultrasonic testing using an ultrasonic testing system from a variety of field of view, similarly to the capability shown in FIG. 1. Also in similar fashion to FIG. 1, a laser beam conditioning system 37 may be used to provide for minimizing the divergence of the laser beam 11 as it exits the end of the Z-mast 47 of this particular embodiment of a gantry positioning system and is delivered to the test object 35. The laser beam conditioning system 37 could likewise be included within the optical transmission channels 22 of the gantry segments of the GPS to provide for conditioning and minimizing the divergence of the beam as it propagates through the GPS. If even more spatial control is desired for directing the laser beam 11 from the end of the Z-mast 47, a rotation attachment platform 49 may be attached to the end of the Z-mast allowing additional directional control and delivering of the laser beam 11 to the test object 35.

Figure 3:
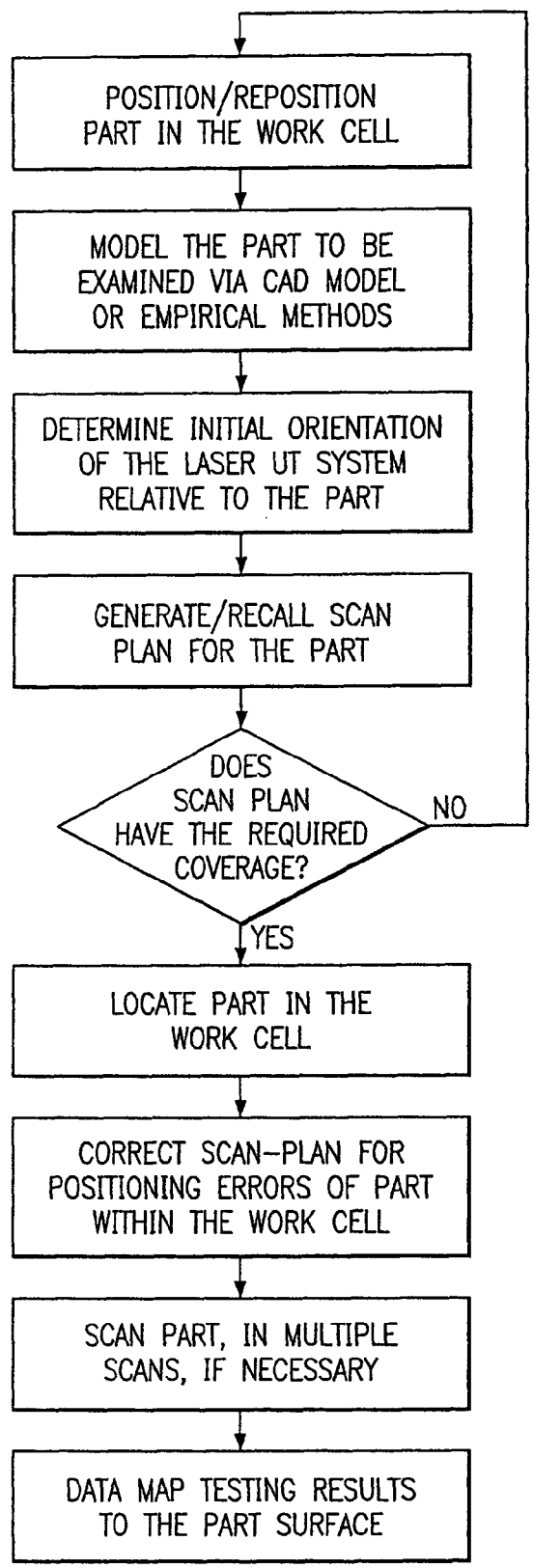
FIG. 3 depicts a flow chart illustrating the method of the present invention.

FIG. 3 depicts a flow chart illustrating the method of the present invention.

The present invention defines robotic position and optical scan-plans for optimum laser ultrasonic testing performance. The optical scan plans can be generated based on the part geometry derived from CAD models, actual measurements, and FIGURE-of-merit parameters defined by laser ultrasonic testing limitations for a particular material type. Requirements may include:

(1) Defining part and fixture orientations in the work cell for repeatable low-cost positioning of the part (this may be a computer defined task based on part CAD models, part center of gravity, holding fixture design, robotic reach, etc. Or it could be a task defined by the system operator where the part location and fixture design is manually defined based on experience);

(2) Maintaining an optimum distance to the part surface based on the system depth-of-field (for example 2.5 m+−0.5 m);

(3) Limiting laser angle of incidence (this will be material dependent, +−45 degrees for some, +−30 for others, also some materials may be extremely specular and on-axis views avoided);

(4) Verifying 100% part coverage with some overlap of scanned regions; and (5) Optimizing throughput by scanning only areas where valid data can be collected with a minimum of robotic repositions.

The present invention has the ability to map laser ultrasonic testing image data. Flat-field laser ultrasonic testing scan data can be projected onto a true 3D surface. This accurately associates ultrasonic data with the true measurement point on the surface. This can be implemented in several ways. First, an integrated measurement system can be used for measuring the surface geometry and providing a one-to-one map between the laser ultrasonic testing data and the measured 3D surface coordinate. Second, the location of the part in the work cell along with the CAD geometry can be used to map the data to the surface. This 3D reconstructed image clearly indicates if the scan coverage is complete and will display proper spatial registration of the individual laser ultrasonic testing scan regions on the part surface.

A second method is not dependent on point-by-point reconstruction based on measured values but instead is concerned with the orientation of the part relative to the laser ultrasonic testing scan view. The principle errors in this method arise from the accuracy that the component is located within the work cell and the positioning/pointing errors of the laser ultrasonic testing sensor.

This provides the benefits of improved data interpretation capabilities, reduced labor cost due to improved analysis features, increased throughput, enhanced testing capabilities for complex structures, and improved archive format for use as reference baseline on subsequent in-service inspections. Potential for automated image comparison directly between different parts or the same part at different service intervals.

The present invention provides a calibration method for 3D beam-pointing. This measurement and calibration procedure corrects for errors in the beam-pointing vector of the laser ultrasonic testing system. This includes all errors due to the 5-axis gantry positioning system and from the optical alignment and pointing of the two-axis optical scanner. This information can be used as required to generated corrected 3D reconstructed images.

Additionally, the present invention provides robotic collision avoidance methods. A collision avoidance system for the pars gantry robot includes the ability to avoid both permanent and temporary objects. Permanent objects include the gantry structure and other fixed hardware inside the work envelope. Temporary objects include parts, part fixtures, and transportation carts.

These provide a significant improvement in avoiding mechanical disaster. Current estimate for downtime due to severe robotic collision is as high as 8 weeks.

Figure 4:
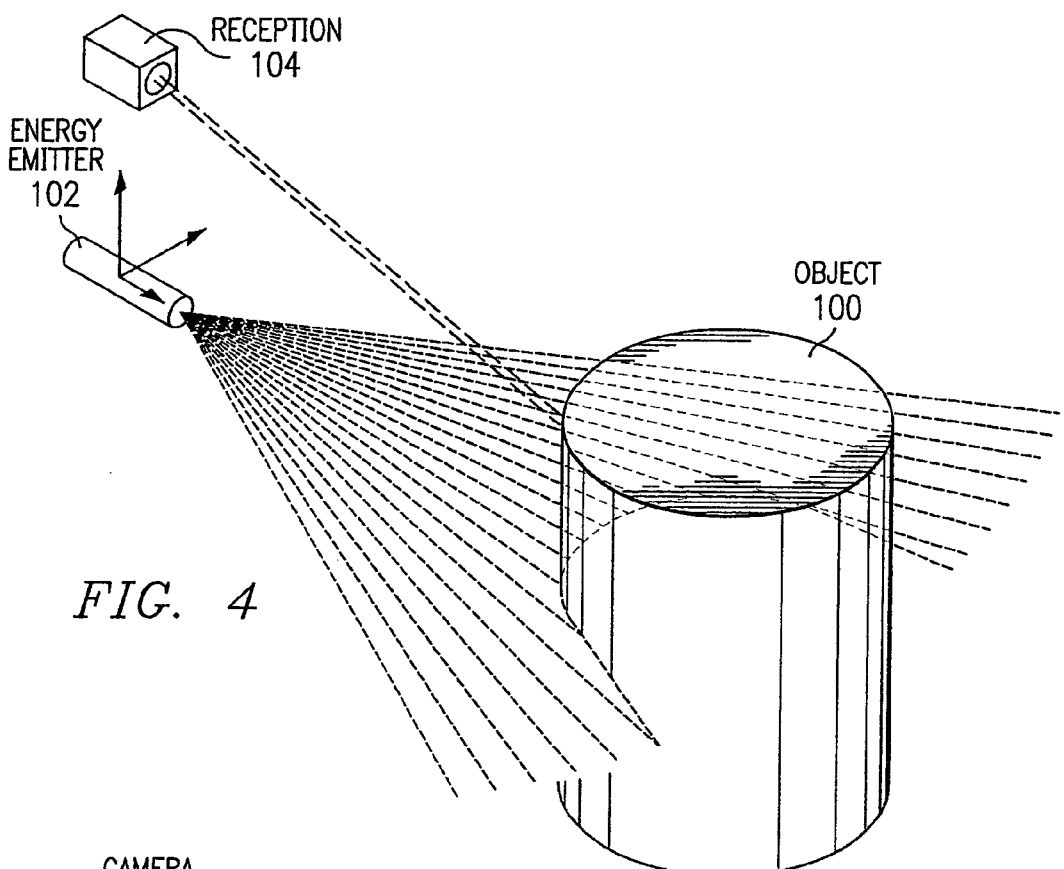
FIG. 4 is a diagram showing the operational units of an embodiment of the invention.

FIG. 4 is a diagram showing the operational units of an embodiment of the invention. An object 100 is to be scanned by the ultrasonic testing system. In the invention, an energy illuminator 102 bathes the object with some form of energy, and an energy reception mechanism that detects energy emanating from the object and associated with the energy imparted by the energy illumination device 102.

The illumination generator and the energy reception mechanism 104 are linked with each other in a predetermined spatial relationship. The predetermined spatial relationship may be fixed, such as being fixed together on one part. Or the relationship may be alterable, with the energy receptive mechanism and the energy illumination generator being present on differing controllable bodies.

In any case, the energy reception mechanism is also associated with the energy generator of the testing mechanism in another predetermined spatial relationship. Again, the predetermined spatial relationship may be fixed, such as being fixed together on one part. Or the relationship may be alterable, with the energy receptive mechanism and the energy illumination generator being present on differing controllable bodies.

The energy illumination generator generates energy and directs it to the object. The energy emanating from the object is detected by the energy receptive mechanism. The characteristics of the emanating energy may be determined, and a precise point on the object may be characterized due to these detected energies.

The energy illumination generator may be a laser, or other type of electromagnetic energy generator, such as a low power radar system. In the case of the radar energy, the energy receptive mechanism can determine the shape of the object, and since the energy receptive mechanism and the energy illumination generator have a predetermined spatial relationship, and another predetermined spatial relationship exists with respect to the energy generation device of the testing system, a precise location in space of the energy generation device may be derived from the measurement.

Relatedly, a sonar type system may be implemented as well. In this case, the energy would be sonic in nature, rather than electromagnetic.

In another embodiment, the energy illumination generator may be a visible light or laser. In this case, the energy receptive mechanism can be a camera, or electronic photo detector. In this manner, the precise position of the energy generation used for ultrasonic testing may be pinpointed in space. This can be accomplished prior to the testing phase, so that efficient sweeps of the object may be performed, or afterwards, such that corrections can be applied to the measurement of the object.

Figure 5:
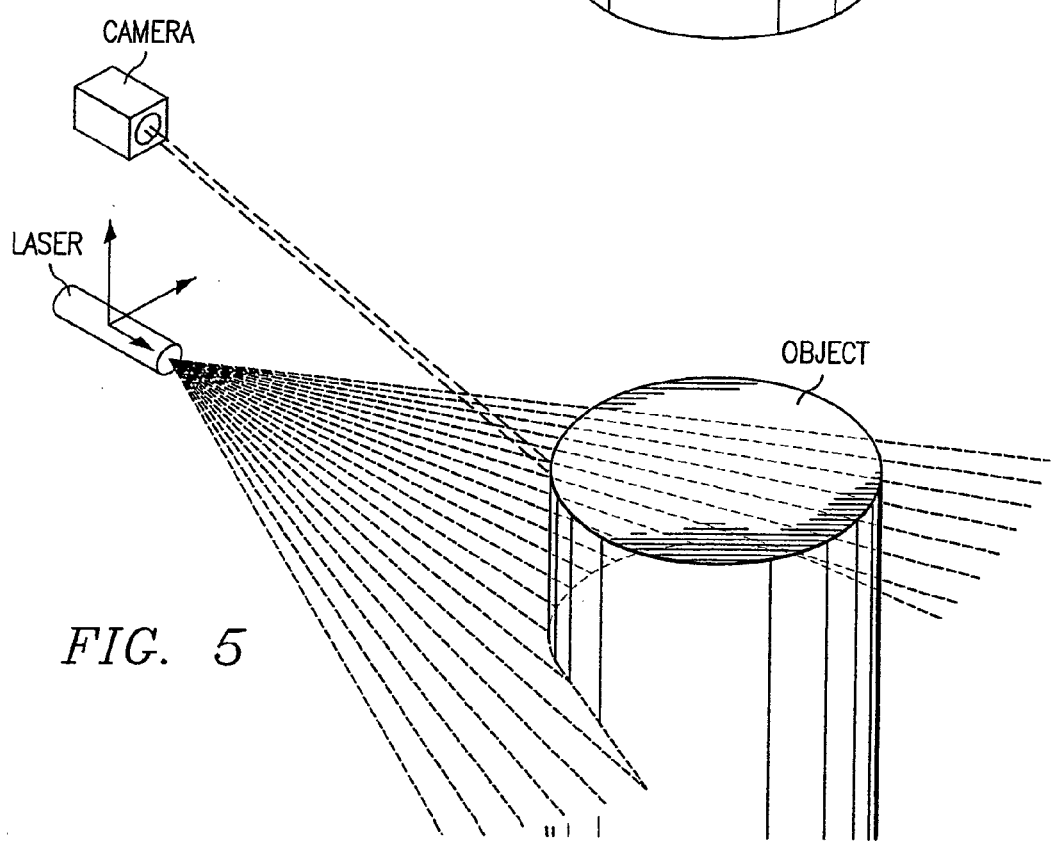
FIG. 5 is a diagram of a specific embodiment of the system of FIG. 4.

FIG. 5 is a diagram of a specific embodiment of the system of FIG. 4. In this embodiment, the energy illuminator is a laser or other type of source of visible electromagnetic energy, and the energy reception mechanism is a camera.

Figure 6:
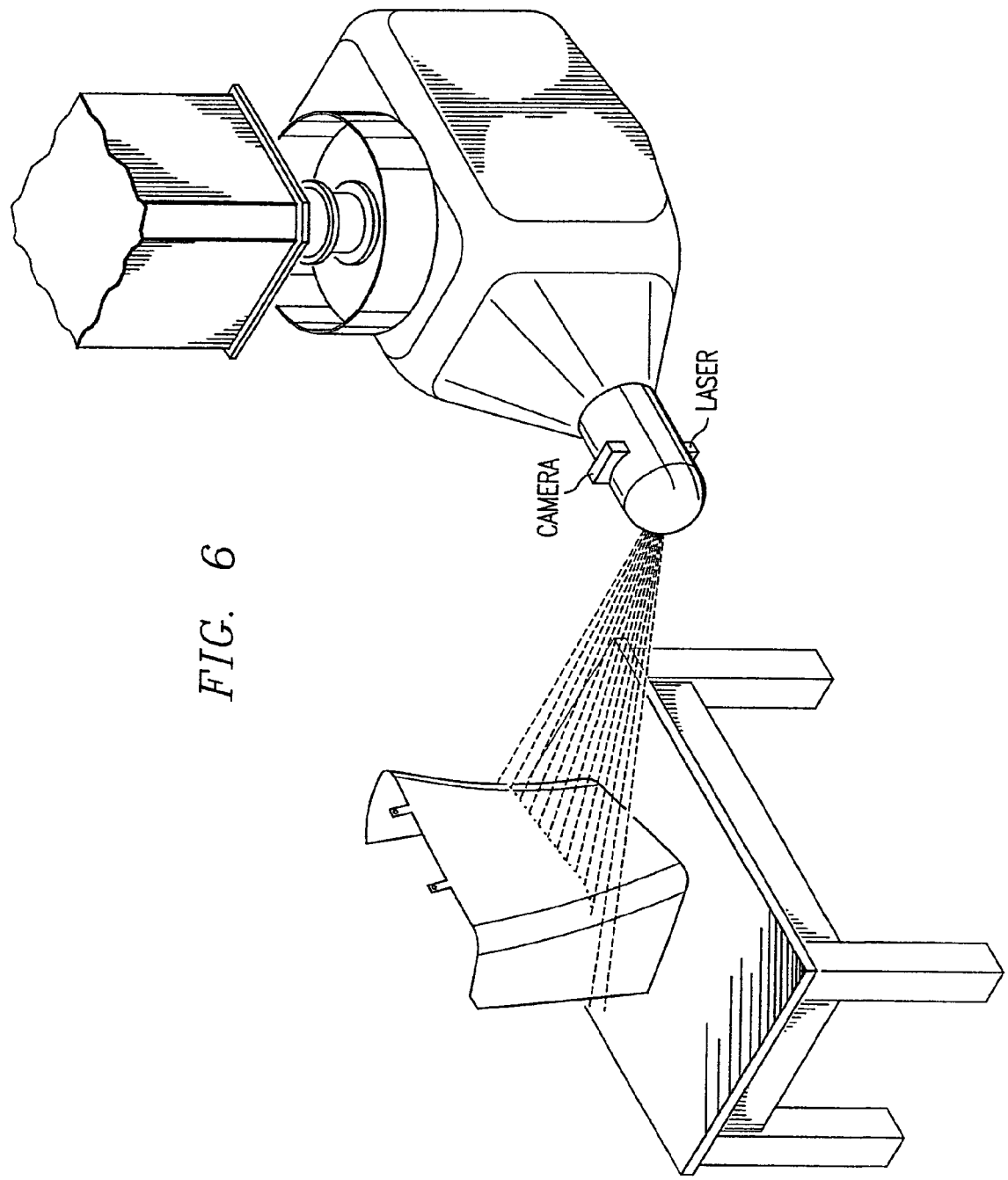
FIG. 6 is a diagram detailing the use of the system of FIG. 4 with a multi-axis laser positioning system.

FIG. 6 is a diagram detailing the use of the system of FIG. 4 with a multi-axis laser generation system. The energy illumination generator laser and the energy receptive mechanism camera are co-located on a laser head that pivots and moves in space. The energy illumination generator laser can be the ultrasonic testing laser, or may be a different sort altogether.

Figure 7:
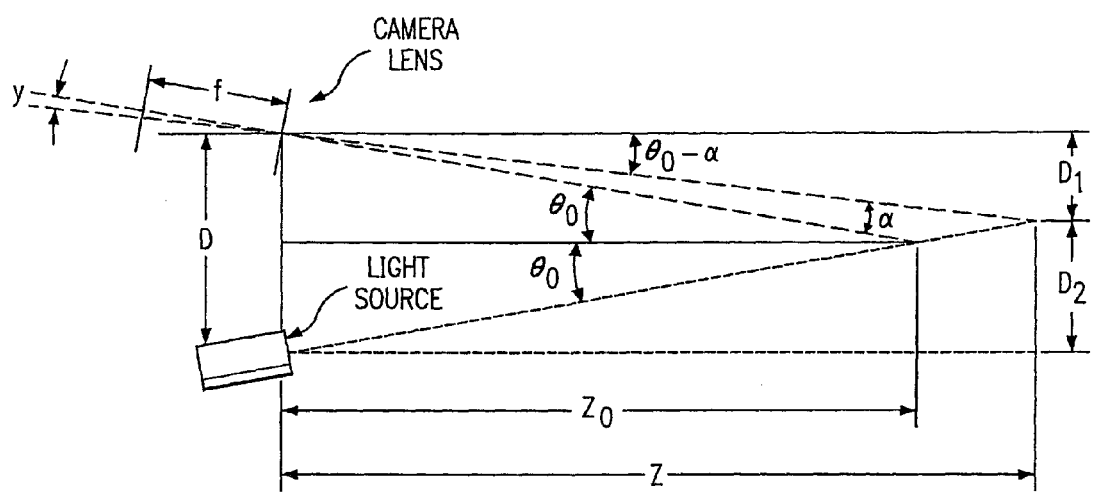
FIGS. 7 and 8 are diagrams detailing the potential relationships inherent in the system of FIG. 4.
Figure 8:
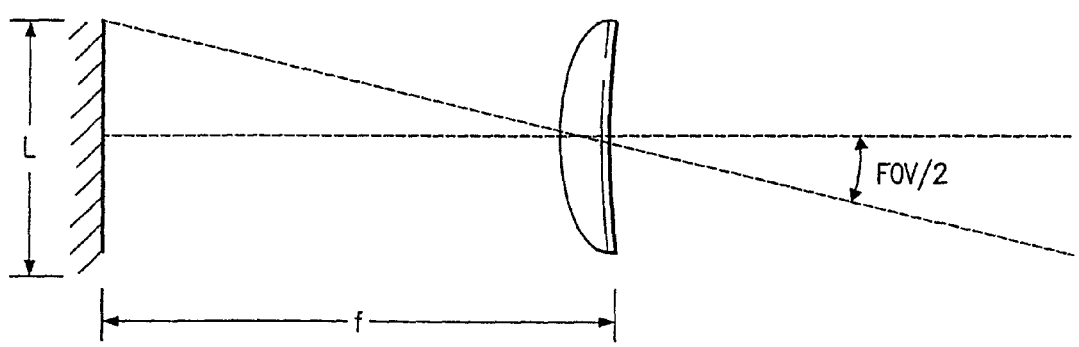

FIGS. 7 and 8 are diagrams detailing the relationships inherent in the system of FIG. 4. FIG. 4 deals mainly with the optical type systems. Other relationships and equations may exist for other types of positioning systems, such as phase reversal equations, time reflectometry equations, and the like.

From the diagram the relationships among the similar triangles yields the following results:

$$\text{TAN}\alpha = \frac{y}{f}$$

$$\text{TAN}\theta_0 = \frac{D_2}{Z} = \frac{D}{2Z_0}$$

$$\text{TAN}(\theta_0 - \alpha) = \frac{D_1}{Z} = \frac{D - D_2}{Z} = \frac{D - \frac{ZD}{2Z_0}}{Z}$$

$$\text{TAN}(\theta_0 - \alpha) = \frac{D - Z\text{TAN}\theta_0}{Z} = \frac{D}{Z} - \text{TAN}\theta_0$$

$$Z = \frac{D}{\text{TAN}(\theta_0 - \alpha) + \text{TAN}\theta_0}$$

$$Z(y) = \frac{D}{\text{TAN}\left[\text{TAN}^{-1}\left(\frac{D}{2Z_0}\right) - \text{TAN}^{-1}\left(\frac{y}{f}\right)\right] + \frac{D}{2Z_0}}$$

This way may derive several relationships. These relationships include:

$$\theta_0 \cong \frac{D}{2Z_0} \text{ AND } a \cong \frac{y}{f} \Rightarrow \text{TAN}(\theta_0 - \alpha) \cong \theta_0 - \alpha$$

$$Z(y) \cong \frac{D}{\frac{D}{Z_0} - \frac{y}{f}} \cong \frac{Z_0}{1 - \frac{yZ_0}{Df}}$$

$$\frac{dZ}{dy} = \frac{-Z_0}{\left[1 - \frac{yZ_0}{Df}\right]^2}\left[-\frac{Z_0}{Df}\right] = \frac{Z_0^2}{Df\left[1 - \frac{yZ_0}{Df}\right]^2}$$

$$dZ = \frac{Z_0^2 dy}{Df\left[1 - \frac{yZ_0}{Df}\right]^2}$$

Thus, several basic equations arise from the optical system thus described. The basic equations are:

$$Z\left[1 - \frac{yZ_0}{Df}\right] = Z_0$$

$$\frac{yZ_0 Z}{Df} = Z - Z_0$$

$$y = Df\left(\frac{1}{Z_0 Z}\right)(Z - Z_0) = Df\left(\frac{1}{Z_0} - \frac{1}{Z}\right)$$

$$dZ(y) = \frac{Z_0^2 dy}{Df\left[1 - \frac{yZ_0}{Df}\right]^2}$$

$$dZ(Z) = \frac{Z_0^2 dy}{Df\left[1 - \left(1 - \frac{Z_0}{Z}\right)\right]^2} = \frac{Z_0^2 dy}{Df\left[\frac{Z_0}{Z}\right]^2} = \frac{Z^2 dy}{Df}$$

$$dZ(Z) = \frac{Z^2 dy}{Df}$$

Thus, in relation to FIG. 8, the following design equations also aid in the determination of the proper system parameters. These include:

$$\text{TAN}\left(\frac{FOV}{2}\right) = \frac{L}{2f}$$

$$FOV = 2\text{TAN}^{-1}\left(\frac{L}{2f}\right)$$

$$dy = \frac{L}{NUM.ELEMENTS}$$

In a numerical example $$L = 0.5'' \text{CCDARRAY} \; FOV \cong 40° \Rightarrow f = 0.68'' (17.3 \text{ mm})$$

$$N = 1024 \Rightarrow dy = \frac{0.5}{2048}$$

$$D = 18''$$

$$dZ(Z) = 2 \times 10^{-5}\left(\frac{1}{in}\right)Z^2$$

$$dZ(60) = 0.072''$$

$$dZ(100) = 0.2''$$

Thus, the optic system of FIGS. 7 and 8 can determine the spatial orientation of the part with a high degree of precision. As such, the results of spatial profiling system can be used in a control circuitry to move relative positions of the object and testing system.

Figure 9:
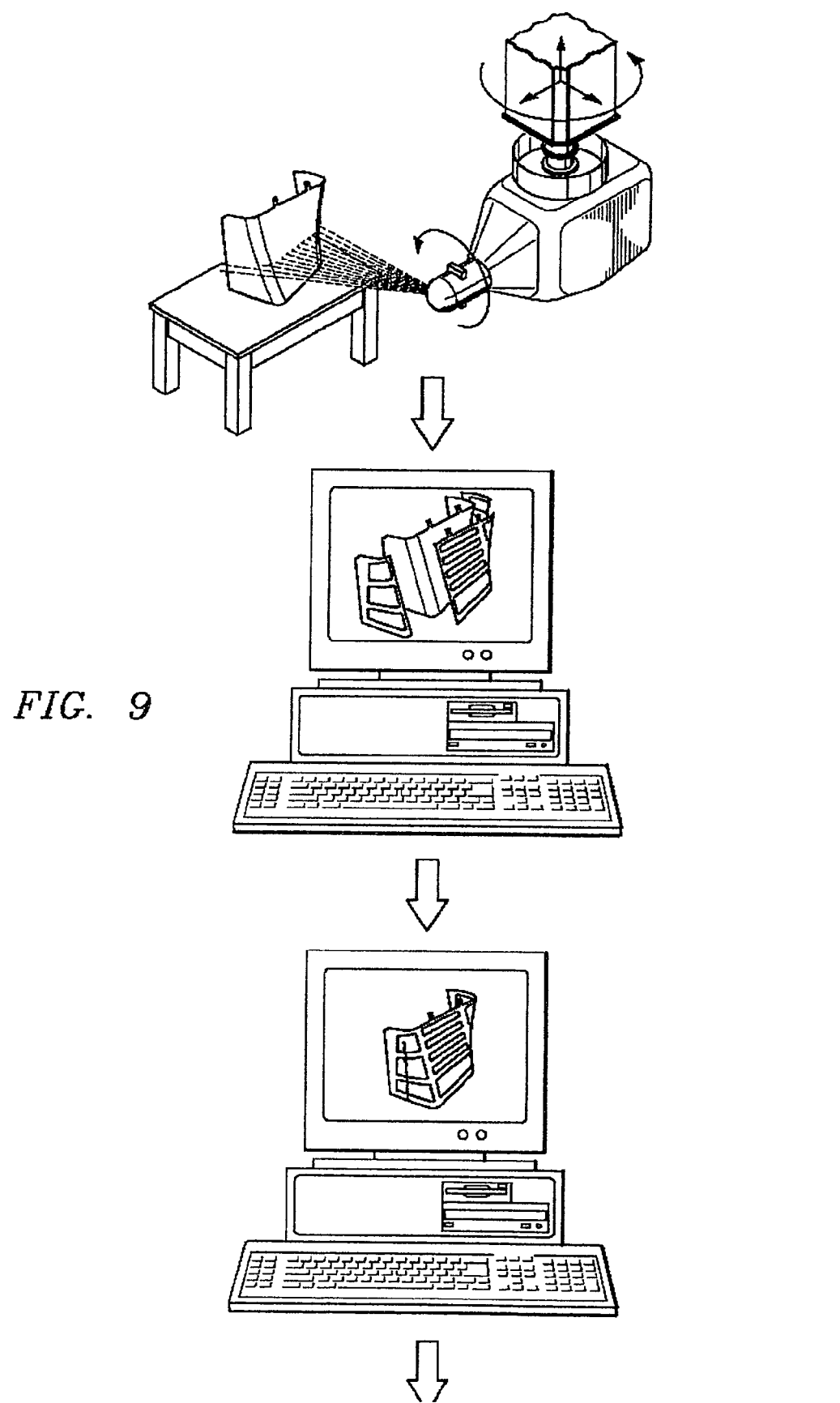
FIG. 9 is a diagram detailing a process of how the system of FIG. 4 can operate.

FIG. 9 is a diagram detailing a process of how the system of FIG. 4 can operate. In one embodiment of the invention, as associated CAD device supplies a representation of the tested part to the system. The head of the laser testing assembly has multiple degrees of kinetic freedom, allowing the head to be positioned very precisely.

In this embodiment, the testing head is placed in proximity with the part to be tested, and the system then determines the proper positioning corrections for the testing to begin. The testing implement is the positioned properly with relation to the object and the testing process begins.

The CAD generated surface is then melded with the testing results. This enables an operator to quickly and easily identify features associated with the tested object, such as faults, stresses, imperfections, and the like. Or, instead of specific points, the testing data may be compared in a scale of acceptable versus unacceptable. In this case, the shaded area might indicate areas that fail to reach threshold testing. This could be used to identify specific manufacturing steps that need to be assessed or changed.

In another related embodiment, the testing of the part may generate results for a specific area of the part, indicated by the shaded area of the first panel of FIG. 8. The entire part may be quickly tested, since the precise positioning mechanism allows the testing system to minimize the overlap associated with specific individual testing actions. This could dramatically increase the speed at which parts are tested.

It should be noted that the system need not position the testing device. The system can be used to position the part, or the testing device, either singly or in combination. The energy illumination generator and the energy receptive mechanism may also exist on separate frames or supports than the positioning system. For example, the energy illumination device and the energy-receiving device may be positioned on supports of the gantry system. This system may move the object within the gantry system or may move the testing device, or both.

It should be noted that this system might be used in any testing system that generates ultrasonic energy. While a laser based system is described, it should be noted that other forms of testing based on reading emitted energy should be encompassed by the invention.

Although the present invention has been described in detail, it should be understood that various changes, substitutions and alterations can be made hereto without departing from the spirit and scope of the invention as described by the appended claims.

What is claimed is:

1. An ultrasonic testing system for detecting features of an object, the system comprising:
    an energy generator, the energy generator producing first energy in the object, the first energy comprising ultrasonic energies;
    an illumination generator that bathes the object with a second energy;
    an energy reception mechanism that receives a third energy emanating from the object;
    the third energy emanating from the object in response to the second energy;
    the illumination generator and the energy reception mechanism coupled to each other in a predetermined spatial relationship;
    the energy reception mechanism associated with the energy generator in a predetermined spatial relationship; and
    control circuitry, communicatively coupled to the energy reception mechanism, that determines the spatial relationship between the object and the energy generator based on the reception of the third energy.

2. The ultrasonic testing system of claim 1, the second energy comprising electromagnetic energy.

3. The ultrasonic testing system of claim 2 wherein the electromagnetic radiation is in the visible light wavelength.

4. The ultrasonic testing system of claim 3 wherein the energy reception mechanism is a camera.

5. The ultrasonic testing system of claim 3 wherein the energy reception mechanism is an array of photoreceptors.

6. The ultrasonic testing system of claim 2 wherein the electromagnetic radiation is coherent electromagnetic energy.

7. The ultrasonic testing system of claim 6, wherein the energy reception mechanism is a camera.

8. An ultrasonic testing system for detecting features on an object, the system comprising:
- a support, that supports the object;
- an energy generator, the energy generator producing first energy in the object, the first energy comprising ultrasonic energies;
- an actuator that changes the relative position of the object relative to the energy generator;
- an illumination generator that bathes the object with a second energy;
- an energy reception mechanism that receives a third energy emanating from the object;
- the third energy emanating from the object in response to the second energy;
- the illumination generator and the energy reception mechanism coupled to each other in a predetermined spatial relationship;
- the energy reception mechanism associated with the energy generator in a predetermined spatial relationship;
- a first control circuitry, communicatively coupled to the energy reception mechanism, that determines the spatial relationship between the object and the energy generator based on the reception of the third energy;
- a second control circuitry, communicatively coupled to the actuator, that changes the spatial relationship between the object and the energy generator based on the reception of the third energy.

* * * * *